United States Patent
Leschinsky

(10) Patent No.: US 6,346,092 B1
(45) Date of Patent: Feb. 12, 2002

(54) INTRA-AORTIC BALLOON CATHETER AND INSERTION SHEATH

(75) Inventor: Boris Leschinsky, Waldwick, NJ (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

(21) Appl. No.: 09/210,922

(22) Filed: Dec. 14, 1998

(51) Int. Cl.[7] ............................................. A61M 29/00
(52) U.S. Cl. .................................................. 604/96.01
(58) Field of Search .......................... 604/96.01, 103, 604/104, 536, 539, 97.1, 97.02, 97.03, 98.01, 98.02, 99.01, 99.02, 101.01, 101.02, 101.03, 101.04, 101.05, 915–921; 606/191–194

(56) References Cited

U.S. PATENT DOCUMENTS

| | | | |
|---|---|---|---|
| 4,608,984 A | 9/1986 | Fogarty | 128/344 |
| 4,710,181 A * | 12/1987 | Fuqua | 604/280 |
| 4,738,666 A * | 4/1988 | Fuqua | 604/280 |
| 5,087,246 A | 2/1992 | Smith | 604/96 |
| 5,158,545 A * | 10/1992 | Trudell et al. | 604/104 |
| 5,195,970 A | 3/1993 | Gahara | 604/96 |
| 5,201,756 A * | 4/1993 | Horzewski et al. | 604/104 |
| 5,226,887 A | 7/1993 | Farr et al. | 604/96 |
| 5,318,588 A * | 6/1994 | Horzewski et al. | 604/104 |
| 5,456,666 A | 10/1995 | Campbell et al. | 604/96 |
| 5,458,572 A | 10/1995 | Campbell et al. | 604/96 |
| 5,458,605 A * | 10/1995 | Klemm | 604/104 |
| 5,458,615 A * | 10/1995 | Klemm et al. | 604/96 |
| 5,681,522 A | 10/1997 | Roychowdhury | 264/532 |
| 6,071,286 A * | 6/2000 | Mawad | 606/108 |
| 6,090,072 A | 7/2000 | Kratoska et al. | |

* cited by examiner

Primary Examiner—Manuel Mendez
(74) Attorney, Agent, or Firm—Abraham Ronai

(57) ABSTRACT

An improved intra-aortic balloon catheter system comprising an insertion sheath, having an expandable distal end, and a tapered balloon membrane capable of being removed through said insertion sheath upon completion of therapy. The outer diameter of the balloon membrane in a wrapped state is smaller than the outer diameter of the outer tube.

21 Claims, 5 Drawing Sheets

INTRA-AORTIC BALLOON CATHETER AND INSERTION SHEATH

BACKGROUND OF THE INVENTION

1. Field of the Invention

The invention relates to an intra-aortic balloon (IAB) catheter. More particularly, the invention relates to an IAB catheter capable of being removed through its insertion sheath.

2. Description of the Prior Art

Intra-aortic balloon (IAB) catheters are used in patients with left heart failure to augment the pumping action of the heart. The catheters, approximately 1 meter long, have an inflatable and deflatable balloon at the distal end. The catheter is typically inserted into the femoral artery and moved up the descending thoracic aorta until the distal tip of the balloon is positioned just below or distal to the left subclavian artery. The proximal end of the catheter remains outside of the patient's body. A passageway for inflating and deflating the balloon extends through the catheter and is connected at its proximal end to an external pump. The patient's central aortic pressure is used to time the balloon and the patient's ECG may be used to trigger balloon inflation in synchronous counterpulsation to the patient's heart beat.

Intra-aortic balloon therapy increases coronary artery perfusion, decreases the workload of the left ventricle, and allows healing of the injured myocardium. Ideally, the balloon should be inflating immediately after the aortic valve closes and deflating just prior to the onset of systole. When properly coordinated, the inflation of the balloon raises the patient's diastolic pressure, increasing the oxygen supply to the myocardium; and balloon deflation just prior to the onset of systole lowers the patient's diastolic pressure, reducing myocardial oxygen demand.

Intra-aortic balloon catheters may also have a central passageway or lumen which can be used to measure aortic pressure. In this dual lumen construction, the central lumen may also be used to accommodate a guide wire to facilitate placement of the catheter and to infuse fluids, or to do blood sampling.

Typical dual lumen intra-aortic balloon catheters have an outer, flexible, plastic tube, which serves as the inflating and deflating gas passageway, and a central tube therethrough formed of plastic tubing, stainless steel tubing, or wire coil embedded in plastic tubing. A polyurethane compound is used to form the balloon.

A great deal of effort has been exerted in an effort to reduce the outer diameter of the IAB catheter. A reduction in size is desired in order to minimize the size of the arterial opening, to facilitate insertion of the catheter into the aorta, maximizing blood flow past the inserted catheter, and also to allow for the use of a smaller insertion sheath to further maximize distal flow. Progress has certainly been made: IAB catheters currently on the market have outer diameters of as low as 8.0 Fr compared to over 10.0 Fr only a few years ago.

Despite the drastic reduction of catheter size, patients undergoing an IAB procedure still suffer a relatively large arterial opening compared to the outer diameter of the IAB catheter. IAB catheters are inserted into the body with the balloon membrane tightly wrapped about the inner tube. The balloon membrane is generally tightly wrapped such that the outer diameter of the wrapped balloon is equal to or slightly larger than the outer diameter of the catheter. Upon removal of the IAB catheter from the patient, however, the balloon membrane is no longer wrapped about the inner tube and cannot be easily removed through the insertion sheath. Thus, removal of the IAB catheter requires removal of the insertion sheath and withdrawal of the IAB catheter directly through the arterial opening. This process may damage the blood vessel or enlarge the arterial opening created during insertion of the IAB catheter. Accordingly, a need exists for a IAB catheter capable of being removed through the same sheath used for its insertion.

One method which is generally used to minimize the size of the balloon membrane prior to removal of the IAB catheter from the patient involves creating a vacuum in the balloon membrane. The reduction in size generated by this method, however, is insufficient to allow withdrawal of the IAB catheter through the insertion sheath.

A similar removal problem has been noted in the angioplasty balloon catheter context and a number of solutions have been posed.

U.S. Pat. Nos. 5,087,246, 5,195,970, 5,226,887, 5,456,666, and 5,458,572, disclose balloon catheters having balloons which collapse into a more readily removable low profile configuration.

U.S. Pat. No. 5,681,522, discloses a balloon catheter having a balloon which was annealed to introduce a memory component into the plastic of the balloon that causes it to assume a lower profile upon deflation then otherwise obtained.

U.S. Pat. No. 4,608,984 discloses a balloon catheter having a second balloon disposed about a first balloon. Said second balloon is used to compress and evacuate the chamber of the first balloon in order to facilitate removal of the catheter.

A catheter capable of being removed through the same insertion sheath as used for its insertion is valuable for another reason besides for its minimization of the arterial size opening. Namely, such a catheter allows a surgeon to leave the insertion sheath in place after removal of the IAB catheter. Upon completion of therapy a surgeon may want to leave the insertion sheath in place until he or she is confident that further therapy will not be required. Similarly, a surgeon, during therapy, may want to switch to a different size IAB catheter or completely replace an inoperative IAB catheter. The present invention obviates the need to reinsert the insertion sheath in these situations.

A need also exists for an IAB catheter which minimizes the amount of arterial insertion site bleeding. The outer diameter of the wrapped balloon membrane of catheters currently on the market is generally larger than the outer diameter of the catheter outer tube. Upon insertion of the IAB catheter the wrapped balloon membrane over dilates the tissue tract and the arterial insertion site beyond the outer diameter of the catheter outer tube. This over dilation creates an annular gap, between the outer surface of the insertion sheath and the tissue tract or between the outer surface of the inserted catheter outer tube and the tissue tract in a sheathless procedure, through which blood escapes during the procedure. Accordingly, a need exists for an IAB catheter whose wrapped balloon membrane does not over dilate the tissue tract and the arterial opening upon insertion beyond the outer diameter of the catheter outer tube.

A need further exists for a sheathlessly inserted IAB catheter capable of being removed without drastically increasing the arterial opening. Similar to percutaneous procedures incorporating sheaths, sheathless procedures also involve the removal of an unfurled balloon membrane.

SUMMARY OF THE INVENTION

Accordingly, it is an object of the invention to produce an intra-aortic balloon catheter capable of being withdrawn through its insertion sheath upon completion of therapy.

It is another object of the invention to produce an insertion sheath capable of having an unfurled intra-aortic balloon membrane withdrawn through it.

It is a further object of the invention to produce a sheathlessly insertable intra-aortic balloon catheter capable of being withdrawn from the artery without significantly increasing the size of the arterial opening.

It is still a further object of the invention to produce an intra-aortic balloon catheter which minimizes arterial bleeding at the insertion site.

It is still yet a further object of the invention to produce an intra-aortic balloon catheter which permits a surgeon the flexibility to leave the insertion sheath in the artery despite removal of the intra-aortic balloon catheter, thus, obviating the need to reinsert the insertion sheath upon reinitiation of therapy or upon replacement of the intra-aortic balloon catheter.

The invention is an improved intra-aortic balloon catheter system comprising an insertion sheath, having an expandable distal end, and a tapered balloon membrane capable of being removed through said insertion sheath upon completion of therapy. The outer diameter of the balloon membrane in a wrapped state is smaller than the outer diameter of the outer tube.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
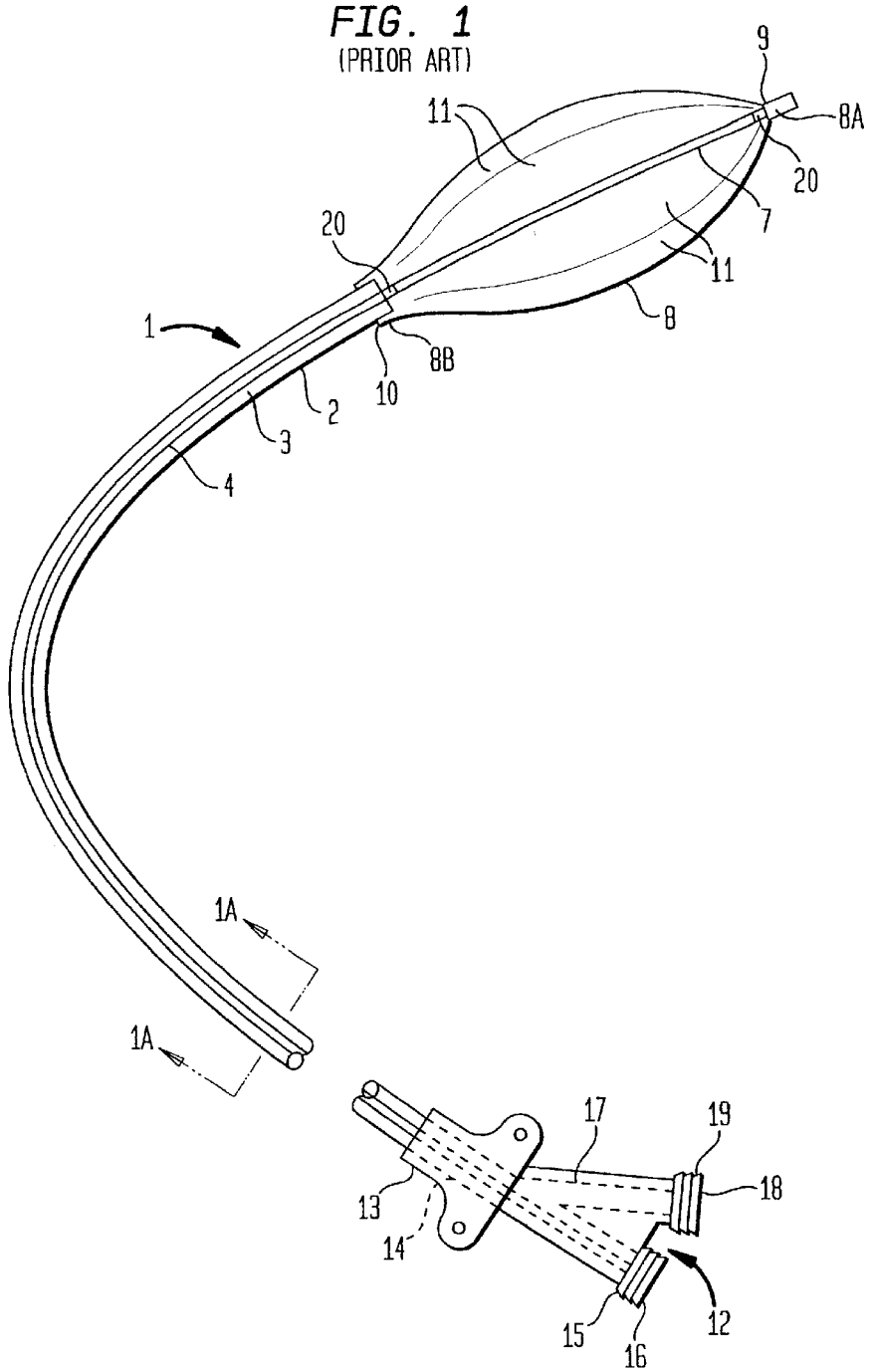
FIG. 1 is longitudinal cross section of a prior art intra-aortic balloon catheter.
Figure 1A:
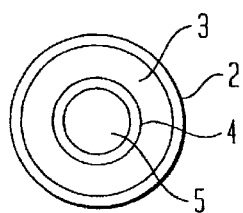
FIG. 1A is a transverse cross section of the prior art intra-aortic balloon catheter taken along line 1A—1A.

The general structure of an intra-aortic balloon catheter is best described in relation to FIGS. 1 and 1A which illustrate a dual-lumen prior art intra-aortic balloon catheter. The catheter 1 is constructed of a plastic outer tube 2 forming a gas passageway lumen 3; and another plastic central tube 4 disposed within outer tube 2 and creating a central passageway or lumen 5 as may best be seen in FIG. 1A.

A balloon 6 is disposed at the distal end of the catheter 1. The distal portion 7 of the central tube 4 extends beyond the distal end 10 of outer tube 2. The distal end 8A of the balloon 8 is attached to a tip 9 formed on the distal end 7 of central tube 4. The proximal end 8B of the balloon 8 is attached, by means of a lap joint, to the distal end 10 of the outer tube 2. The distal portion 7 of the central tube 4 supports the balloon 8. Said distal portion 7 must have sufficient strength to prevent inversion of the balloon 8 as it inflates and deflates under aortic pressure, but at the same time, be flexible enough to be safely inserted through an introducer sheath, moved through the arterial tree, and maintained in the thoracic aorta.

The balloon 8 is formed of a nonthrombogenic flexible material, such as polyurethane, and may have folds 11 formed as a result of wrapping the balloon 8 about the central tube 4 to ease insertion of the catheter 1. The balloon 8 has a single wall thickness of between 3 to 6 mils. Radio-opaque bands 20 at the distal end of the catheter 1 aid in positioning the balloon 8 in the descending aorta.

Inflation and deflation of the balloon 8 is accomplished through the gas passageway lumen 3. The central passageway or lumen 5 can accommodate a guide wire for placement or repositioning of the catheter 1. When the guide wire is not disposed in the central lumen 5, the central lumen 5 may be used for measuring blood pressure in the descending aorta. This pressure measurement may be used to coordinate the inflation and deflation of the balloon 8 with the pumping of the heart, however, use of the patient's ECG is preferred. Additionally, the central lumen 5 may be used to infuse liquids into the descending aorta, or to sample blood.

At the proximal end 12 of the catheter 1 a hub 13 is formed on the proximal end 14 of the outer tube 2. The central passageway or lumen 3 extends through the hub 13 and a connector 16 is provided at the proximal end 15 (or exit) of the central passageway or lumen 3. Measurement of aortic pressure and blood sampling may be done through the proximal end 15 of the central passageway 3.

The proximal end 18 of the gas passageway or lumen 3 exits through a side arm 17 of the hub 13 on which is provided a connector 19. The proximal end 18 of the gas passageway or lumen 3 may be connected to an intra-aortic balloon pump.

Figure 2A:
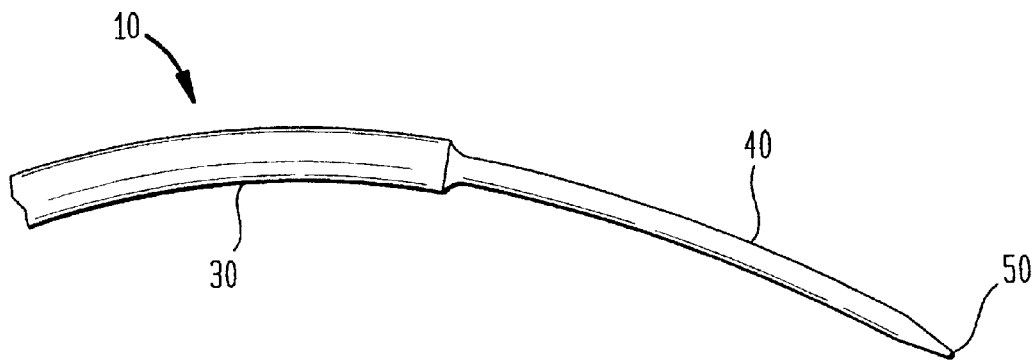
FIG. 2A is a side view of a distal portion of the improved intra-aortic balloon catheter with the balloon in a folded/compact state.
Figure 2:
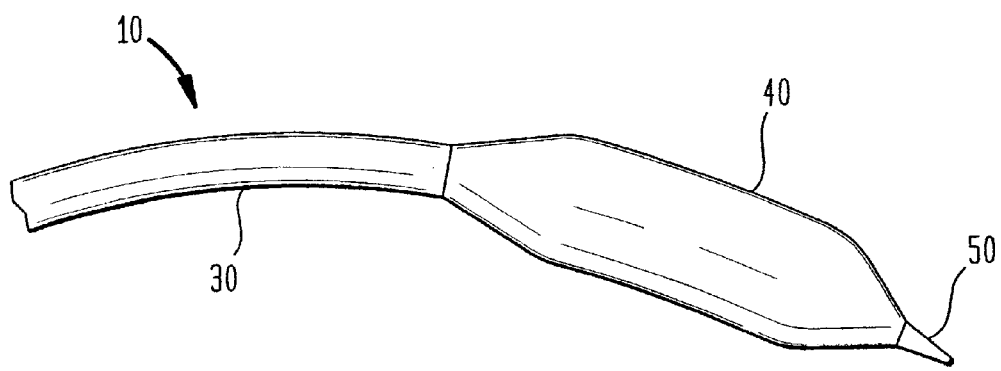
FIG. 2 is a side view of a distal portion of an improved intra-aortic balloon catheter having a tapered balloon membrane.
Figure 3:
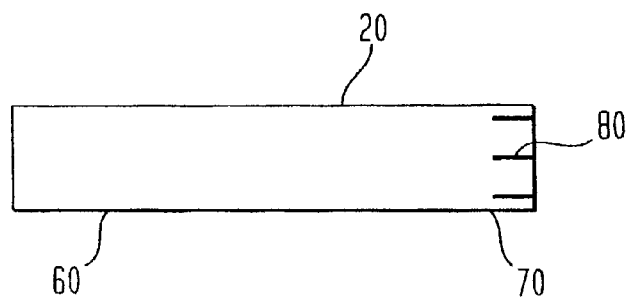
FIG. 3 is a side view of an improved insertion sheath having a scored end.

The present invention comprises an improved intra-aortic balloon catheter system incorporating an improved intra-aortic balloon (IAB) catheter 10, as illustrated in FIG. 2, and an improved insertion sheath 20, as illustrated in FIG. 3. FIG. 2 illustrates a side view of a distal portion of the improved intra-aortic balloon catheter 10 comprising an outer tube 30, a balloon membrane 40 having proximal and distal ends, a tip 50, and an inner tube (not shown) having proximal and distal ends. The distal ends of the balloon membrane 40 and the inner tube are attached to the tip 50. The proximal end of the balloon membrane 40 is attached to the distal end of the outer tube 30. The balloon membrane 40 of the present invention and the balloon membranes of prior art balloons are similar in that they both have a taper on either end of the balloon membrane 40. The balloon membrane 40 of the present invention, however, has a gradual proximal end taper capable of being pulled through the distal end of the insertion sheath 20 in an unfurled state. This feature is important because it facilitates the process of withdrawing an unfurled balloon membrane 40 in the body of a patient through the insertion sheath 20, thus preventing a patient's arterial opening from enlarging upon withdrawal of the IAB catheter 10 along with its unfurled balloon membrane 40. The degree of taper of the proximal end of the balloon membrane 40 will depend on the size, geometry, and structure of the distal end of the insertion sheath 20 through which the unfurled balloon membrane 40 is to be withdrawn.

In the preferred embodiment of the invention, the outer diameter of the wrapped balloon membrane 40 should be less than the outer diameter of the outer tube 30 (see FIG. 2A). This difference in diameter of the wrapped balloon membrane 40 relative to the outer tube 30 allows for greater clearance between the unfurled balloon membrane 40 and the insertion sheath 20 or the arterial opening in a sheathless procedure. Generally, IAB catheters are designed such that the outer diameter of the wrapped balloon membrane 40 is either the same or greater than the outer diameter of the outer tube 30. This design scheme is consistent with the goal of creating an IAB catheter with the smallest effective outer diameter and also consistent with the fact that it is typically easier to design an outer tube 30 of reduced diameter than it is to design an IAB catheter 10 having a reduced diameter wrapped balloon membrane 40. Generally, as soon as technology is available to reduce the outer diameter of the wrapped balloon an IAB catheter is designed having an outer tube with an identical or smaller outer diameter. Thus, use of an outer tube 30 having a larger outer diameter than that of the wrapped balloon membrane 40, given the availability of a smaller outer tube, is typically not considered. However, as demonstrated above use of such an arrangement facilitates retraction of the unfurled balloon membrane 40 upon completion of therapy.

Figure 5:
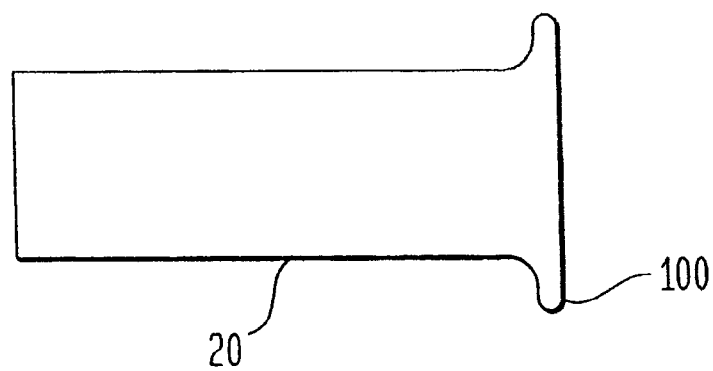
FIG. 5 is a side view of an insertion sheath having a lip.
Figure 6:
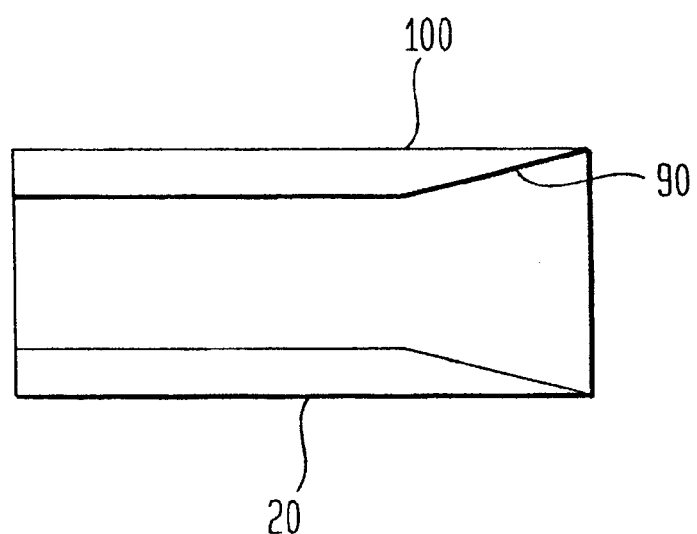
FIG. 6 illustrates a longitudinal cross section of the insertion sheath wherein the inner surface of the distal end has a truncated cone shape.

The distal end of the insertion sheath 20 may be made from an expansible material allowing said end to expand and funnel the unfurled balloon membrane 40 into the insertion sheath 20. FIGS. 3, 5, and 6 illustrate three specific embodiments of insertion sheaths.

Figure 3A:
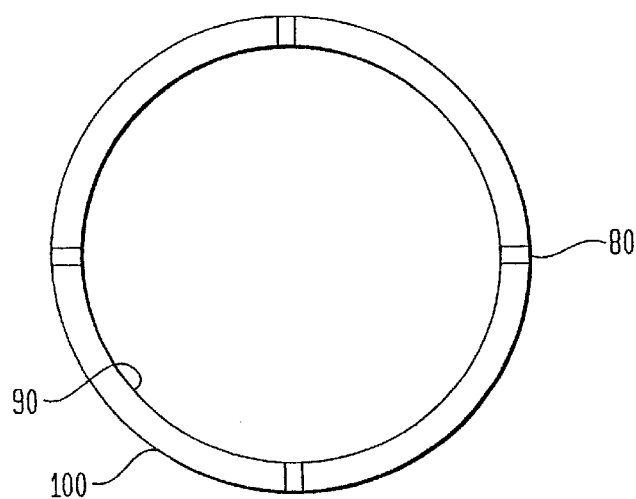
FIG. 3A is a front view of the scored end of the improved insertion sheath.
Figure 3B:
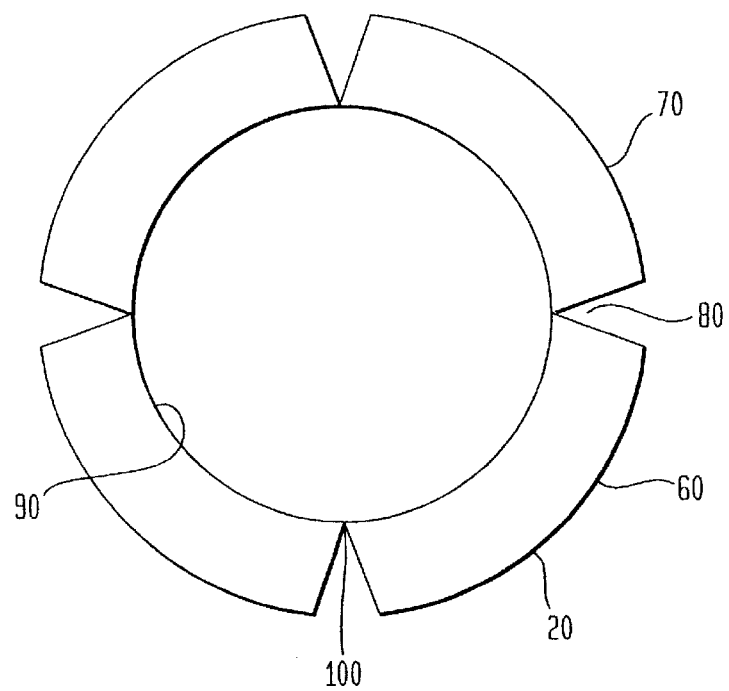
FIG. 3B is a front view of the scored end of the improved insertion sheath, of FIG. 3A, in a flared state.

FIG. 3 illustrates a side view of the improved insertion sheath 20 comprising a scored tube 60 having a scored end 70. Said scored end 70 having longitudinal scores 80 spaced radially along its circumference. FIG. 3A illustrates a front view of the scored end 70. Application of a threshold pressure within the scored end 70 causes it to flare open as illustrated in FIG. 3B. As indicated above, the insertion sheath 20 may be made from an expansible material, thus, the insertion sheath 20 may dilate beyond that permitted by the flaring of the distal end.

Figure 4:
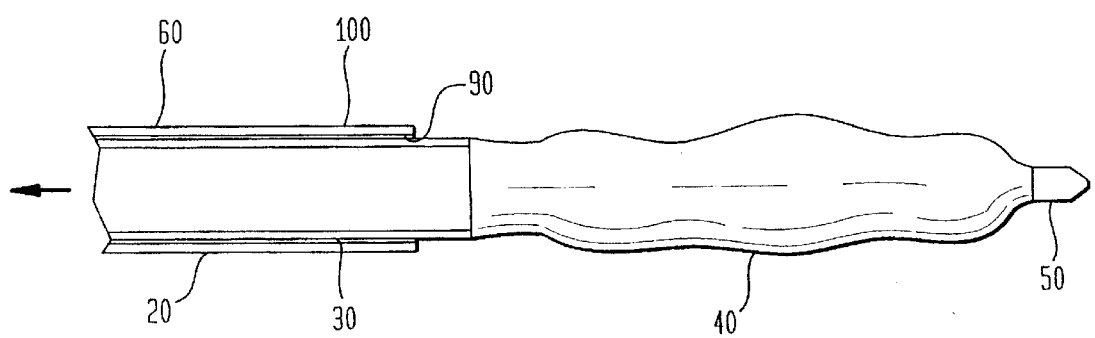
FIG. 4 is longitudinal cross sectional view of the intra-aortic balloon catheter being withdrawn through the insertion sheath upon completion of a procedure.
Figure 4A:
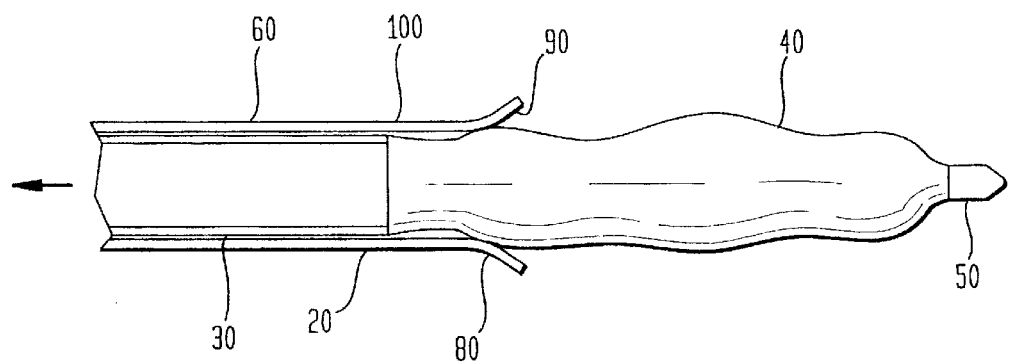
FIG. 4A is longitudinal cross sectional view of the intra-aortic balloon catheter withdrawn through the insertion sheath to the point that scores on the distal end of the insertion sheath begin to flare.

FIGS. 4 and 4A illustrate withdrawal of the improved IAB catheter 10 through the insertion sheath 20. FIG. 4 illustrates the proximal end of the balloon membrane 40 being pulled through the distal end of the insertion sheath 20. The arrow indicates the direction the IAB catheter 10 is being pulled. At this point, there is no contact between the scored end 70 and the balloon membrane 40. Further withdrawal of the unfurled tapered balloon membrane 40 through the scored end of the insertion sheath 20 gradually dilates the scored end 70 of the scored tube 60. FIG. 4A illustrates the insertion sheath 20 after the IAB catheter 10 has been further withdrawn through the insertion sheath 20. The balloon membrane 40 makes contact with the scored end 70 of the scored tube 60 and forces the scored end 70 into the configuration illustrated in FIG. 3A. Thus, the scored end 70 acts as a funnel preventing the unfurled balloon membrane from becoming snagged on the distal end of the insertion sheath 20. Upon withdrawal of the insertion sheath 20 from the patient the vasculature of the patient forces the scores 80 back to their original configuration, as illustrated in FIG. 3A, allowing for a smooth removal of the insertion sheath 20.

The scores 80 on the scored tube 60 may comprise longitudinal slots which penetrate the scored tube 60. Alternatively, the scores 80 may be deep grooves in an inner surface 90 or an outer surface 100 of the scored tube 60 which allow the scored end 70 to take on the configuration illustrated in FIG. 3B upon sufficient internal pressure being applied in the scored end 70 by the balloon membrane 40.

FIG. 5 illustrates an alternative embodiment of the insertion sheath 20 having a lip 110. The lip 110 guides the unfurled tapered balloon membrane 40 into the insertion sheath 20 upon withdrawal of the IAB catheter 10 from the patient. As indicated above, the insertion sheath 20 may be made from an expansible material, thus, the insertion sheath 20 may dilate to an outer diameter greater than the outer diameter of the lip 110.

FIG. 6 illustrates the third specific embodiment of the insertion sheath 20. The inner surface 90 of the distal end of the insertion sheath 20 may have a truncated cone shape, as illustrated in FIG. 6, to facilitate entrance of the unfurled balloon membrane into the insertion sheath 20.

It should be noted that the insertion sheath 20 of the present invention may be used with other medical devices which require the withdrawal of an unfurled balloon membrane through an opening in a body lumen.

What is claimed is:

1. A balloon catheter comprising an outer tube, a tip, and a balloon membrane, a proximal portion of the balloon membrane is attached to the outer tube and a distal portion of the balloon membrane is connected to the tip, said balloon membrane is inserted into a body lumen in a wrapped state, the outer diameter of a substantial portion of the balloon membrane in its wrapped state is smaller than the outer diameter of the outer tube.

2. The balloon catherer as claimed in claim 1 wherein the balloon membrane is capable of being pulled through a distal end of an insertion sheath, a distal end of said insertion sheath having one or more scores.

3. The balloon catherer as claimed in claim 1 wherein the balloon membrane is capable of being pulled through a distal end of an insertion sheath, a distal end of said insertion sheath being expansible.

4. The balloon catheter as claimed in claim 1 wherein the balloon membrane has a taper such that the balloon membrane in a deflated state can be pulled through a distal end of an insertion sheath.

5. An insertion sheath for a medical device, said medical device having a balloon membrane which is inserted in a compact state into a body lumen and which can be pulled through a distal end of an insertion sheath in a secondary state larger than the compact state it was originally inserted in, said insertion sheath having proximal, medial, and distal sections, said medial section being substantially non-expensible, said distal section being expansible so as to allow withdrawal of the medical device with the balloon membrane in the secondary state.

6. The insertion sheath as claimed in claim 5 comprising a tube having a one or more scores on its distal end.

7. A method for removing a balloon catheter from a body lumen after use of said balloon catheter, said balloon catheter being inserted into a vessel through an insertion sheath, said balloon catheter comprising an outer tube and a balloon membrane, at least a proximal portion of said balloon membrane is attached to the outer tube, said insertion sheath having proximal, medial, and distal sections, said medial section being substantially non-expansible, said distal section being expansible, said method comprising pulling the balloon catheter through a distal end of the insertion sheath with sufficient force so as to expand the distal end of the insertion sheath and pull the balloon catheter through the medial section of the insertion sheath.

8. The method as claimed in claim 7 wherein the balloon membrane has a taper on a proximal end.

9. The method as claimed in claim 7 wherein the balloon catherer further comprises a tip connected to a distal end of the balloon membrane.

10. The balloon catherer as claimed in claim 1 wherein the balloon catherer is an intra-aortic balloon catherer and wherein a distal end of the balloon membrane and the outer tube are connected to a tip.

11. The balloon catheter as claimed in claim 3 wherein the distal end of the insertion sheath is expansible.

12. The balloon catheter as claimed in claim 3 wherein the distal end of the insertion sheath has one or more scores.

13. The balloon catheter as claimed in claim 1 wherein the balloon membrane is capable of being pulled through a distal end of an insertion sheath having an inner surface, a distal end of said inner surface having a truncated cone shape.

14. The balloon catherer as claimed in claim 1 further comprising a tip and an inner tube disposed within an outer surface of the outer tube, the tip, a distal end of the balloon membrane, and a distal end of the inner tube are connected.

15. The balloon catherer as claimed in claim 1 wherein the balloon membrane is capable of being pulled through a distal end of an insertion sheath having an outward lip.

16. An insertion sheath for a medical device, said medical device having an outer tube and a balloon membrane at least partially attached to said outer tube, said medical device being inserted in a compact state into a body lumen, an inner surface of a distal end of the insertion sheath having a truncated cone shape which allows the medical device to be pulled through a distal end of the insertion sheath in a state larger than the compact state it was originally inserted in.

17. The insertion sheath as claimed in claim 16 wherein the medical device is an intra-aortic balloon catheter, the insertion sheath is tubular, and the balloon membrane is folded in the compact state.

18. An insertion sheath for a medical device, said medical device having an outer tube and a balloon membrane at least partially attached to said outer tube, said medical device being inserted in a compact state into a body lumen, a distal end of the inesertion sheath having an outward lip so as to allow the medical device to be pulled through a distal end of the insertion sheath in a state larger than the compact state it was originally inserted in. compact state it was originally inserted in, a distal end of the insertion sheath has an outward lip.

19. The insertion sheath as claimed in claim 18 wherein the medical device is an intra-aortic balloon catheter, the insertion sheath is tubular, and the balloon membrane is tubular in the compact state.

20. The method as claimed in claim 7 wherein the insertion sheath comprises a tube having one or more scores on a distal end.

21. The method as claimed in claim 7 wherein the balloon catherer further comprises a tip and an inner tube disposed within an outer surface of the outer tube, the tip, a distal end of the balloon membrane, and a distal end of the inner tube are connected.

* * * * *